United States Patent [19]

Kay

[11] Patent Number: 4,826,658

[45] Date of Patent: May 2, 1989

[54] CONTACT LENS CLEANING AND DISINFECTION

[76] Inventor: Joseph B. Kay, 17 Long Close, Farnham Common, Slough, Berkshire, Great Britain

[21] Appl. No.: 51,467

[22] PCT Filed: Jun. 16, 1986

[86] PCT No.: PCT/GB86/00348

§ 371 Date: Apr. 14, 1987

§ 102(e) Date: Apr. 14, 1987

[87] PCT Pub. No.: WO86/07264

PCT Pub. Date: Dec. 18, 1986

[30] Foreign Application Priority Data

Jun. 14, 1985 [GB] United Kingdom ................ 8515079

[51] Int. Cl.⁴ .............................................. A61L 2/16
[52] U.S. Cl. ....................................... 422/30; 422/28; 422/29; 422/292; 424/613; 514/840
[58] Field of Search ................... 422/28, 30, 292, 29, 422/119; 424/130; 514/840

[56] References Cited

U.S. PATENT DOCUMENTS

| | | |
|---|---|---|
| 3,912,451 | 10/1975 | Gaglia . |
| 3,919,048 | 11/1975 | Dahlmans et al. ................ 435/177 |
| 3,954,965 | 5/1976 | Boghosian et al. ............. 514/840 X |
| 4,585,488 | 4/1986 | Giefer ............................ 252/174.12 |
| 4,588,586 | 5/1986 | Kessler et al. .................. 424/130 X |
| 4,670,178 | 6/1987 | Huth et al. ...................... 514/840 X |

FOREIGN PATENT DOCUMENTS 0139994  5/1985  European Pat. Off. .
2104242  2/1983  United Kingdom .

*Primary Examiner*—Barry S. Richman
*Assistant Examiner*—Jill Johnston
*Attorney, Agent, or Firm*—Nixon & Vanderhye P. C.

[57] ABSTRACT

A method of disinfecting a contact lens using hydrogen peroxide, which method comprises conducting the hydrogen peroxide treatment of the lens in the presence of an immobilized enzyme which catalyses the decomposition of hydrogen peroxide. The invention also provides apparatus and a kit for treating contact lens. Preferably the enzyme is catalase, which may be immobilized by adsorption, by absorption, by covalent binding or by antibody complexing.

14 Claims, 1 Drawing Sheet

CONTACT LENS CLEANING AND DISINFECTION

FIELD OF THE INVENTION

This invention relates to a method and apparatus for cleaning and disinfecting contact lenses and, in particular, to a method and apparatus for neutralizing the potentially toxic residues left after the cleaning and disinfection of contact lenses.

BACKGROUND AND SUMMARY OF THE INVENTION

Hydrogen peroxide is widely used to clean and disinfect contact lenses, normally generated in situ from effervescing tablets containing sodium percarbonate and citric acid. Hydrogen perioxide is effective for this purpose but any excess hydrogen peroxide can cause ocular irritation when the contact lens is re-inserted into the eye. To remove such excess hydrogen peroxide, repeated washings and rinsings of the lens are necessary but this is unacceptable in the case of soft contact lenses since undesirable leaching of isotonic solutions from the lenses can occur. An alternative procedure that has been suggested is to neutralize the hydrogen peroxide by chemical means e.g. by treating the solution with slowly released sodium nitrite or sodium sulphite. such a method however has the disadvantage of leaving the neutralizing chemicals in the lens-treating solution which may themselves cause ocular irritation.

European Published Patent Application No. 0082798A discloses a regime for the treatment of contact lenses by disinfecting and cleaning them with a hydrogen peroxide solution and then treating with catalase, firstly by adding catalase to the hydrogen peroxide solution, secondly by pouring off the hydrogen peroxide solution and adding a catalase solution or by transferring the lenses to another vessel containing a catalase solution.

The methods disclosed in that European published patent application possess the severe disadvantage that the use of catalase as a solution requires the solution to be preserved; this means that extraneous preservative is in contact with the lenses and may therefore require its own removal regime before the lenses may be safely inserted into the eyes of a wearer.

According to a first aspect of the present invention there is provided a method of treating a contact lens by means of hydrogen peroxide, which method comprises conducting the hydrogen peroxide treatment of the lens in the presence of an immobilized enzyme which catalyses the decomposition of hydrogen peroxide.

According to a second aspect of the present invention there is provided a method of decomposing hydrogen peroxide used for treating a contact lens which method comprises contacting the hydrogen peroxide with an immobilized enzyme which catalyzes the decomposition of hydrogen peroxide.

According to a further aspect of the present invention there is provided apparatus for treating contact lenses with hydrogen peroxide which apparatus includes an effective amount of an immobilized enzyme capable of catalyzing the decomposition of hydrogen peroxide. The apparatus may comprise a container bearing a suitable quantity of a said immobilized enzyme.

BRIEF DESCRIPTION OF THE DRAWING

The accompanying

DETAILED DESCRIPTION OF THE INVENTION

Figure 1:
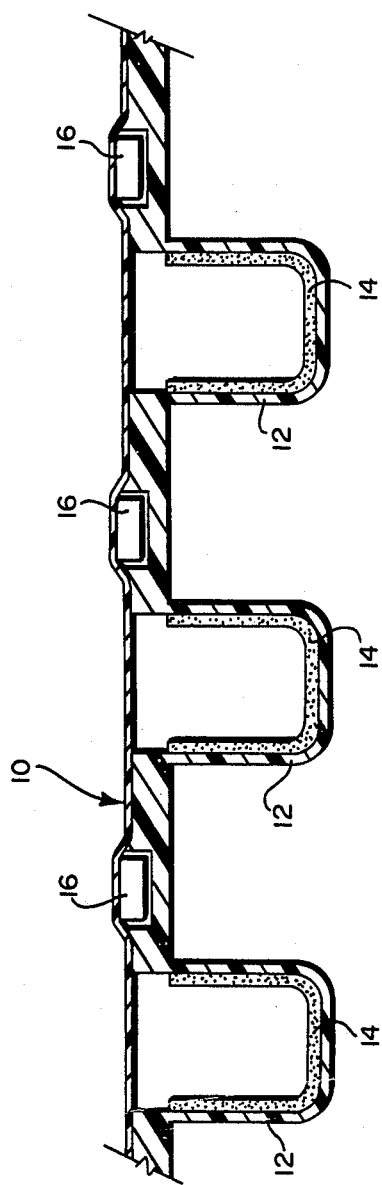
FIG. 1 shows, in a partial cross-sectional schematic view, an embodiment of the present invention whereby plural separable vials are provided with an appropriate hydrogen peroxide release agent.

The enzyme capable of causing the decomposition of hydrogen peroxide, generally known as a peroxidase, is preferably catalase although any other suitable enzyme may be employed for the purpose.

Immobilization of the enzyme may be by any of the techniques appropriate for this purpose. Such techniques include binding of the enzyme to a support material e.g. by adsorption, by absorption or by chemical (e.g. covalent) binding. Examples of surfaces upon which the enzyme may be adsorbed include alumina, bentonite, calcium phosphate gels. carbon, plastics, carboxymethyl cellulose, carboxymethylsephadex, collagen, glass and silica gel. The adsorbent surfaces may be continuous e.g. a coating upon the inside of a container or the actual material of which a said container is composed. The adsorbent surface may constitute the surface of a plurality of fixed beads or of a fixed disc or discs or the interstices of a fixed sponge or fritt.

Examples of materials to which the enzyme may be covalently bound include supports with -OH, (e.g. cellulloses) supports with $-NH_2$ (e.g. epoxy resins), supports with $CO_2H$ (e.g. methacrylates methacrolates) and supports containing anhydrides.

A preferred surface upon which to immobilize the enzyme has been found to be the surface of a plastics material such as polystyrene, activated e.g. by gamma irradiation u.v. light or by corona discharge. Simple coating of the activated plastics surface with enzyme may suffice for the purposes of the present invention.

As in the case of adsorbent surfaces, the supports may be a coating upon the surface of a container or the material of which a containers is composed, etc.

Very preferably however the enzyme is immobilized by use of an antibody. By this we means that the enzyme is complexed with an antibody which regards the enzyme as an antigen and the complex is coated by means of the complexed antibody onto a suitable support surface. Preferably the support surface used in this and in the foregoing embodiments is the inner surface of a plastics container the surface of which may have been pretreated by u.v. light, corona discharge, irradiation, etc. to improve the coating ability of the enzyme or complexed enzyme.

A suitable antibody may be obtained e.g. by injecting enzyme into a mouse and collecting resultant antibodies generated by the mouse immune-response system. The antibodies may be arranged by appropriate biotechnological techniques to be monoclonal in nature, e.g. by use of suitable hybridomas.

By way of example only, embodiments of the present invention will now be described.

EXAMPLE 1

Catalase is injected into suitable selected mice and antibodies to the catalase are collected from the mice, concentrated and purified. The catalase and the antibody are then contacted together in vitro to prepare a catalase-antibody complex. This complex is then coated onto the inner walls and base of a plastics contact lens container.

The container so-coated may then be dried and stored in a sterile environment until required. Alternatively the coated container may be filled with a sterilized aqueous phase e.g. buffered saline solution and stored until required.

The container preferably has means e.g. a screw threaded upper portion for receiving a lid provided with means for holding a contact lens.

To prepare the solution of hydrogen peroxide for treating a said contact lens, an aqueous phase e.g. insolonic buffered saline is placed in the container and an effervescent table containing sodium percarbonate and citric acid added to the aqueous phase. The aqueous phase may be such that the resultant solution contains hydrogen peroxide at a 0.1 Molar concentration and is substantially isotonic.

The hydrogen peroxide is present in solution in sufficient quantity (e.g. 0.1 Molar) to clean and disinfect the contact lens within a period of from a few minutes to a few hours. The complexed enzyme is present in a sufficient amount to cause decomposition of the hydrogen peroxide within a period of from say ½ hour to 8 hours. By this means substantially all excess hydrogen peroxide will be decomposed and substantially none of the enzyme will enter the aqueous phase and thus problems of ocular irritation or hypersensitization will be substantially avoided.

EXAMPLE 2

A 10 ml polystyrene container or vial is irradiated with 2.5 Megarads of gamma irradiation to activate its surface. Into the containers is placed a solution of catalase powder in water at a concentration of 0.5 mg/ml (catalase activity: 24,000 units per milligram where 1 unit decays 1 micromole of hydrogen peroxide per minute at 25° C.) and the filled container is then incubated at room temperature for 24 hours. Thereafter the vial is emptied, rinsed gently with distilled water and allowed to dry at room temperature.

The dried, coated vial may then be stored for extended periods without significant loss of activity. For example it has been found that such vials remain effective even after storage at 45° C. for 3 months.

To such a dried, enzyme-coated vial there is added an aqueous hydrogen peroxide solution containing from 0.6 to 3% by volume of hydrogen peroxide. A moderator, phenolphthalin, is also added to indicate the progess of hydrogen peroxide decomposition. It is found that after ½ hour no detectable hydrogen peroxide remains.

The present invention provides a method and apparatus of treating a contact lens which mitigates the disadvantages of known contact lens treatment regimes.

The present invention also consists in a kit for treating contact lenses, which may include an enzyme-coated container as hereinbefore defined, a hydrogen peroxide release agent and a suitable aqueous phase. The coated containers may be arranged to be disposable single use items and more for example be supplied in sealed blister- or bubble-packs for removal and use as desired.

The hydrogen peroxide release agent may be for example a table or capsule containing sodium phosphate and citric acid, which table or capsule may also contain an indicator, sufficient sodium chloride to render the residual solution isotonic and may also contain, if desired, an agent for removing free chlorine from the solution.

In a preferred embodiment of the apparatus of the present invention a strip 10 of commuted plastics vials 12 is provided, each vial 12 being separable from the remainder and each coated internally with the enzyme 14 (shown in greatly enlarged manner for clarity of presentation). The vials 12 may be disposed of after each has been used once. The vials 12 may be accompanied by predetermined quantities of the hydrogen peroxide release agent 16, e.g. in the form of pellets, prills or granules.

It will be apparent that although what has been described above is the use of an immobilized enzyme capable of causing the decompostion of hydrogen peroxide, the invention is not limited to the use solely of such an immobilized enzyme. The invention covers the use generally of immobilized enzymes to treat contact lenses. For example proteolytic emzymes are currently used to remove protein deposits from contact lenses but are used as solutions. The present invention embraces the case where such a proteolytic enzyme is, for example, coated onto the wall of a contact lens treatment container. Such immobilization will substantially eliminate the well-known problem of ocular hypersensitization due to the use of free proteolytic enzyme.

The invention also covers all such changes and modifications to the method, apparatus and kit as would be apparent to one skilled in the art.

I claim:

1. A method of disinfecting a contact lens, which method comprises treating the lens with a solution of hydrogen peroxide having a strength sufficient to disinfect the lens, and decomposing the residual hydrogen peroxide in the solution by exposure thereof to an enzyme which catalyses the decomposition of hydrogen peroxide, wherein the enzyme is immobilized to a surface in the solution and, whereby the hydrogen peroxide is decomposed without the need for removal from the solution of the enzyme.

2. A method according to claim 1, wherein the enzyme is catalase.

3. A method according to claim 1 or 2, wherein the enzyme is adsorbed onto a surface.

4. A method according to claim 3, wherein the surface is that of a container for the treating solution.

5. A method according to claim 3, wherein the surface is formed of plastic.

6. A method according to claim 5, wherein the plastic has been activated by irradiation by corona discharge, or by u.v. light.

7. A method according to claim 1 or 2, wherein the enzyme is covalently bound to a surface in the solution.

8. A method according to claim 1 or 2, wherein an antibody is coated on a surface in the solution, and the enzyme is complexed with the antibody.

9. A method according to claim 8 wherein the antibody is mouse anti-catalase antibody.

10. A kit for disinfecting a contact lens comprising;
a kit means containing
a container for a contact lens;
a solution having an amount of a hydrogen peroxide release agent adapted to provide an effective concentration of hydrogen peroxide in the container to disinfect the contact lens; and
an effective amount of an enzyme immobilized to a surface of the container and capable of catalyzing the decomposition of hydrogen peroxide, wherein said effective amount of hydrogen peroxide may be decomposed by means of the enzyme without the need for removing the enzyme from the solution.

11. The kit according to claim 10 wherein the container is composed of irradiated polystyrene.

12. The kit according to claim 10 wherein the container includes a plurality of disposable vials each containing a quantity of said immobilized enzyme.

13. The kit according to claim 10, wherein said hydrogen peroxide release agent is present as granules or in table or capsule form.

14. The kit according to claim 10 wherein said hydrogen peroxide release agent further includes at least one of sodium chloride in an amount sufficient to render residual solution isotonic, an indicator for indicating the presence or absence of hydrogen peroxide, and an agent capable of removing free chlorine from aqueous solution.

* * * * *